(12) United States Patent
Korkeamäki (10) Patent No.: US 10,709,824 B2
(45) Date of Patent: Jul. 14, 2020

(54) ACCESSORY PART

(71) Applicant: Serres Oy, Kauhajoki as. (FI)

(72) Inventor: Rami-Matti Korkeamäki, Kauhajoki (FI)

(73) Assignee: Serres Oy, Kauhajoki as. (FI)

( * ) Notice: Subject to any disclaimer, the term of this patent is extended or adjusted under 35 U.S.C. 154(b) by 346 days.

(21) Appl. No.: 15/328,932

(22) PCT Filed: Aug. 6, 2015

(86) PCT No.: PCT/FI2015/050517
§ 371 (c)(1),
(2) Date: Jan. 25, 2017

(87) PCT Pub. No.: WO2016/020577
PCT Pub. Date: Feb. 11, 2016

(65) Prior Publication Data
US 2017/0216500 A1 Aug. 3, 2017

(30) Foreign Application Priority Data

Aug. 7, 2014 (FI) .................................... 20145708

(51) Int. Cl.
*A61M 1/00* (2006.01)
*A61L 2/18* (2006.01)
*B08B 9/08* (2006.01)
*B65D 51/24* (2006.01)

(52) U.S. Cl.
CPC .............. *A61M 1/0005* (2013.01); *A61L 2/18* (2013.01); *A61M 1/0017* (2014.02); *B08B 9/0804* (2013.01); *B65D 51/24* (2013.01); *A61M 2209/10* (2013.01)

(58) Field of Classification Search
CPC .............. A61M 1/0005; A61M 1/0017; A61M 2209/10; A61L 2/18; B08B 9/0804; B65D 51/24
See application file for complete search history.

(56) References Cited

U.S. PATENT DOCUMENTS

| 3,809,577 A | 5/1974 | Thorsson |
| 5,185,007 A | 2/1993 | Middaugh et al. |
| 5,527,272 A | 6/1996 | Folden |

(Continued)

FOREIGN PATENT DOCUMENTS

| DE | 19750093 C1 | 2/1999 |
| EP | 0390094 | 3/1990 |

(Continued)

OTHER PUBLICATIONS

PCT Written Opinion of the International Searching Authority, dated Dec. 16, 2015; 6 pages.

(Continued)

*Primary Examiner* — Tinsae B Ayalew
(74) *Attorney, Agent, or Firm* — Seyfarth Shaw LLP (57) ABSTRACT

The invention relates to an accessory part to be used in connection with cleaning a suction bag emptying device (13), the accessory part comprising a lid (25) for closing a container (15) in the emptying device (13), and a capsule containing agent to be used for cleaning the emptying device (13) in connection with the lid (25). The invention further relates to a suction bag emptying device (13).

4 Claims, 9 Drawing Sheets

(56) References Cited

U.S. PATENT DOCUMENTS

| | | |
|---|---|---|
| 5,807,359 A | 9/1998 | Bemis |
| 5,954,958 A | 9/1999 | Folden |
| 6,652,495 B1 | 11/2003 | Walker |
| 2012/0292346 A1* | 11/2012 | Watson ................. D06F 39/022 |
| | | 222/185.1 |

FOREIGN PATENT DOCUMENTS

| | | |
|---|---|---|
| EP | 0390094 A1 | 10/1990 |
| EP | 0667140 A2 | 8/1995 |
| GB | 1348474 A | 3/1974 |
| JP | S49-025025 B | 6/1974 |
| JP | H03-047257 A | 2/1991 |
| JP | 2002-516578 A | 6/2002 |
| WO | 0124846 A1 | 4/2001 |

OTHER PUBLICATIONS

Supplementary European Search Report, dated Feb. 22, 2018; 2 pages.
Japanese Office Action for Application No. 2017-506295 dated May 16, 2019, 4 pages.

* cited by examiner

ACCESSORY PART

CROSS REFERENCE TO RELATED APPLICATIONS

This is a National Stage application of PCT/FI2015/050517, filed Aug. 6, 2015, which claims priority to Finland Patent Application No. 20145708, filed Aug. 7, 2014, the disclosures of which are incorporated herein by reference.

BACKGROUND OF THE INVENTION

The invention relates to an accessory part used in connection with cleaning a suction bag emptying device. The invention also relates to a suction bag emptying device.

BRIEF DESCRIPTION OF THE INVENTION

An object of the invention is to provide an easy-to-use accessory part for an emptying device.

Advantages of the accessory part according to the invention include the part being easy to use and there being no need to dispense any cleaning agent or touch any cleaning agent in connection with cleaning the suction bag emptying device. There is no need to construct a separate cleaning agent supply system for the emptying device either. A further advantage of an embodiment of the invention is that the cleaning agent can be made last longer than usual in connection with a cleaning process.

The accessory part is a lid supported by the rim of the emptying device or by a holder at the rim, in connection with which there is a capsule containing agent to be used for cleaning the suction bag emptying device. The agent to be used for cleaning the suction bag emptying device is usually liquid cleaning agent but it may also be gel or powder. The capsule is a container provided in connection with the lid. In other words, the capsule may be above or below the lid or inside the lid. The capsule may be a container formed in the lid, there being a space inside the container for the agent, usually liquid, to be used for cleaning the emptying device. The agent in the container is enclosed inside the lid in such a way that it cannot exit without breaking the lid. Instead of cleaning agent, the agent to be used for cleaning the emptying device may be disinfectant.

The container may be closed with a plug extending to the inside of the container in such a way that the plug displaces liquid agent. In other words, when a given amount of liquid agent has been put in the container, the container is closed with a plug, the plug being pressed near the bottom of the container, which results in the liquid level rising in a circular area in the container around the plug. Between the end of the plug and the bottom of the container, there remains a gap through which the liquid can flow. At the bottom of the container, in the area remaining under the plug, there may be ridges extending radially from the middle of the container towards the edges and ensuring that the plug cannot get too deep but that the gap is always open. Using the above-described structure for the capsule makes the liquid agent last longer than usual because the gap between the plug and the bottom of the container throttles the flow to be suitably small.

In an operating situation, the accessory part is placed upon the rim of the container in the emptying device, or against the possible holder at the rim of the container, usually in the same way as a suction bag when the emptying of the suction bag is started. A member for puncturing the lid in the suction bag emptying device, usually a conical head at the end of a cylinder, is pressed through the accessory part, i.e. the lid containing liquid agent intended for cleaning. The capsule is broken and the liquid agent begins to flow along the cylinder and its conical head, reaching, at the conical head, openings from where water or other liquid or gas is flowing. The liquid agent is mixed into the flow arriving from the openings and becomes thus uniformly dispensed into the flow.

BRIEF DESCRIPTION OF THE FIGURES

The invention will now be described in more detail in connection with preferred embodiments and with reference to the accompanying drawings, in which.

DETAILED DESCRIPTION OF THE INVENTION

Figure 1:
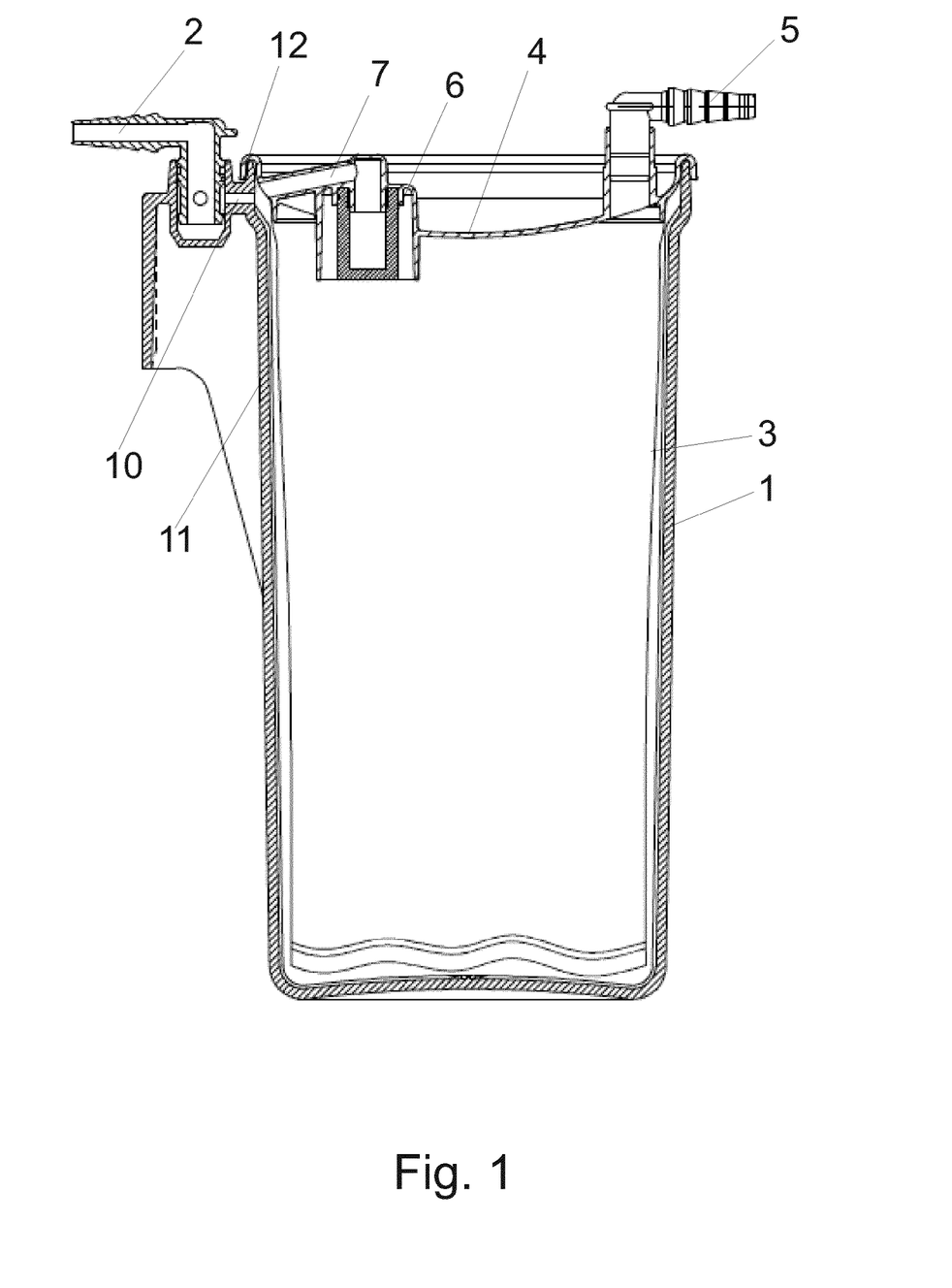
FIG. 1 shows a cross section of a suction bag arrangement.
Figure 2:
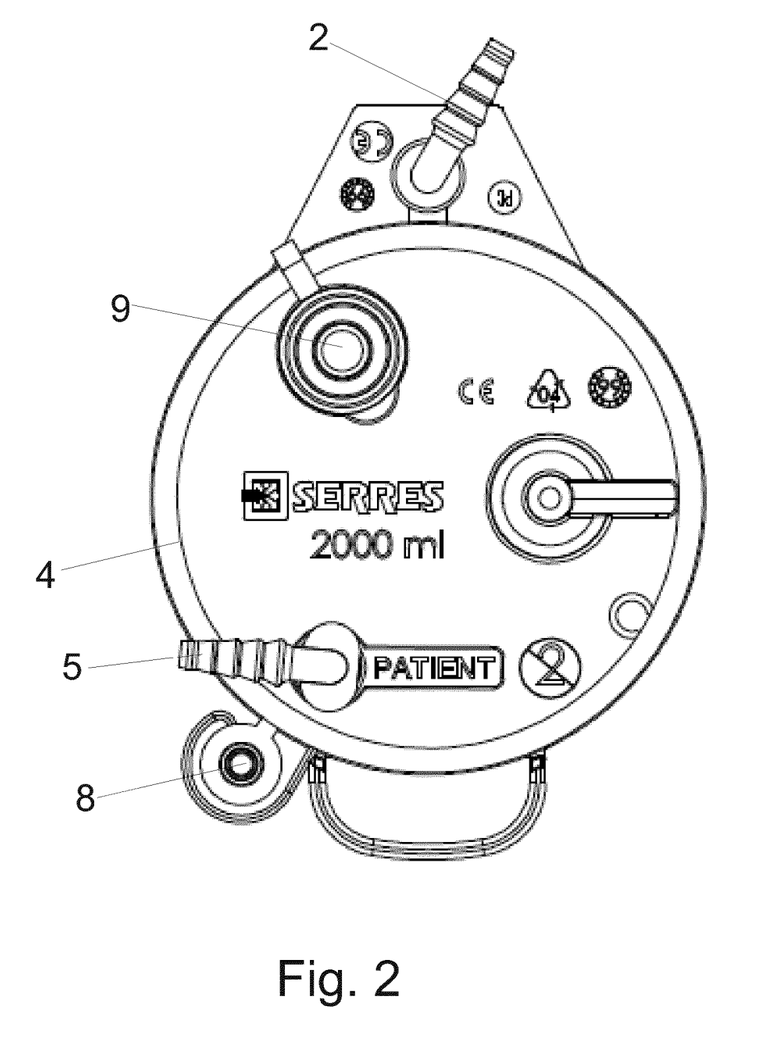
FIG. 2 shows a top view of a suction bag arrangement.

FIGS. 1 and 2 first disclose the structure and operation of a suction bag 3. The suction bag of FIGS. 1 and 2 is an example of a suction bag suitable to be emptied by an emptying device shown in FIGS. 3 to 6.

In accordance with what is shown in FIG. 1, the suction bag arrangement comprises a collection reservoir 1 that is open at one end, a suction bag 3 that may be arranged in the collection reservoir 1 and comprises a flexible bag portion that is fixedly fastened to a lid 4. The collection reservoir 1 is provided with a fitting 2, which is in flow connection with a source of negative pressure, and a channel 10 for producing a negative pressure in an area 11 between the inner surface of the collection reservoir 1 and the outer surface of the suction bag 3. The lid 4 is provided with a patient fitting 5 for connecting a patient hose for fluid to the inner part of the suction bag 3, and the lid 4 has a channel 7 for transmitting negative pressure from a space between the inner surface of the collection reservoir 1 and the lid 4 into the inner part of the suction bag 3 as well as a filter 6 for preventing impurities from entering the suction system. The filter 6 is fastened to the lid surface on the inner side of the suction bag 3, and the lid 4 is a uniform piece.

FIG. 2 is a top view of the suction bag arrangement. In addition to the parts disclosed in FIG. 1, FIG. 2 shows a plug 8 integrated in the lid 4 for closing the patient fitting 5 after use, and a fitting 9 used for connecting suction bag arrangements in series, for taking samples and for emptying.

An emptying device is shown in FIGS. 3 to 6. An emptying device 13 comprises a container 15 provided with a lid 14. The lid 14 is usually hinged to the container 15. The container 15 has a holder, in this case a shoulder 16, and a discharge point 17. The lid 14 is provided with means for puncturing the suction bag lid and for supplying pressurized liquid or gas into the suction bag to be emptied. In the case of FIGS. 3 to 6, the above-mentioned means are formed by a hollow cylinder 19 provided with a blunt conical head 18.

The cylinder 19 has openings 21 through which the pressurized liquid or gas flows into the suction bag 3. The means for puncturing the suction bag lid and for supplying the pressurized liquid or gas into the suction bag to be emptied may be implemented in various other ways, too. Instead of the hollow cylinder 19 with a blunt conical head 18, a hollow cylinder with a cutting edge, for example, may be used, or a cone with a fixed pointed head that punctures the lid 4 of the suction bag 3, openings being provided in the cone above the pointed head to allow liquid or gas to flow.

Figure 3:
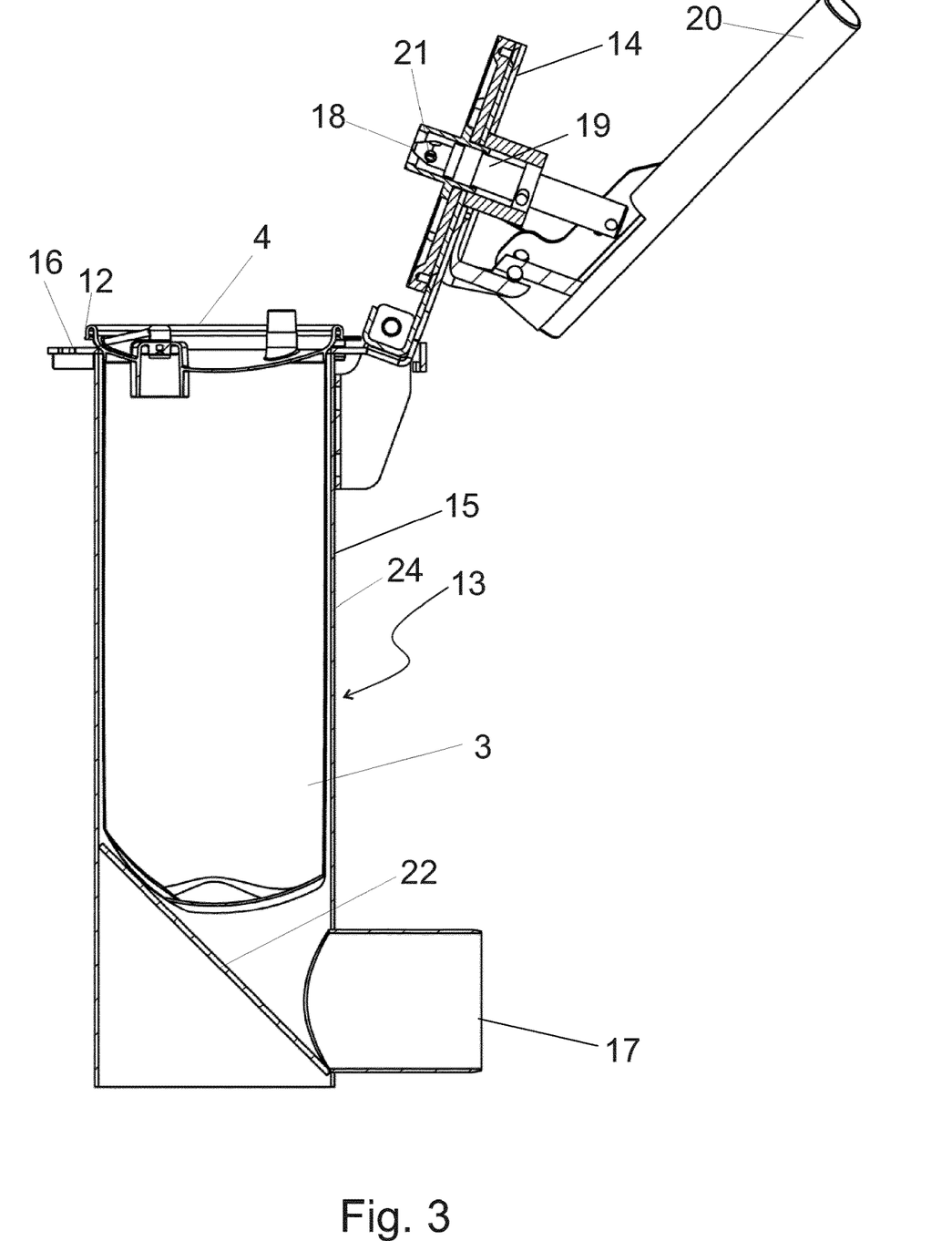
FIGS. 3 to 6 show cross sections of a suction bag emptying device and a suction bag.

When it is emptied, the suction bag 3 is placed in the container 15 in such a way that the rim 12 or rim area of the lid 4 becomes set against the shoulder 16. The 'rim area' refers to the circular area inside the rim 12. The container 15 is preferably dimensioned in such a way that its height from the bottom of the container to the holder is greater than the length of the suction bag. Consequently, the bottom of the suction bag 3 does not touch the bottom of the container 15. In other words, the suction bag 3 hangs from the shoulder 16, as shown in FIG. 3.

Figure 4:
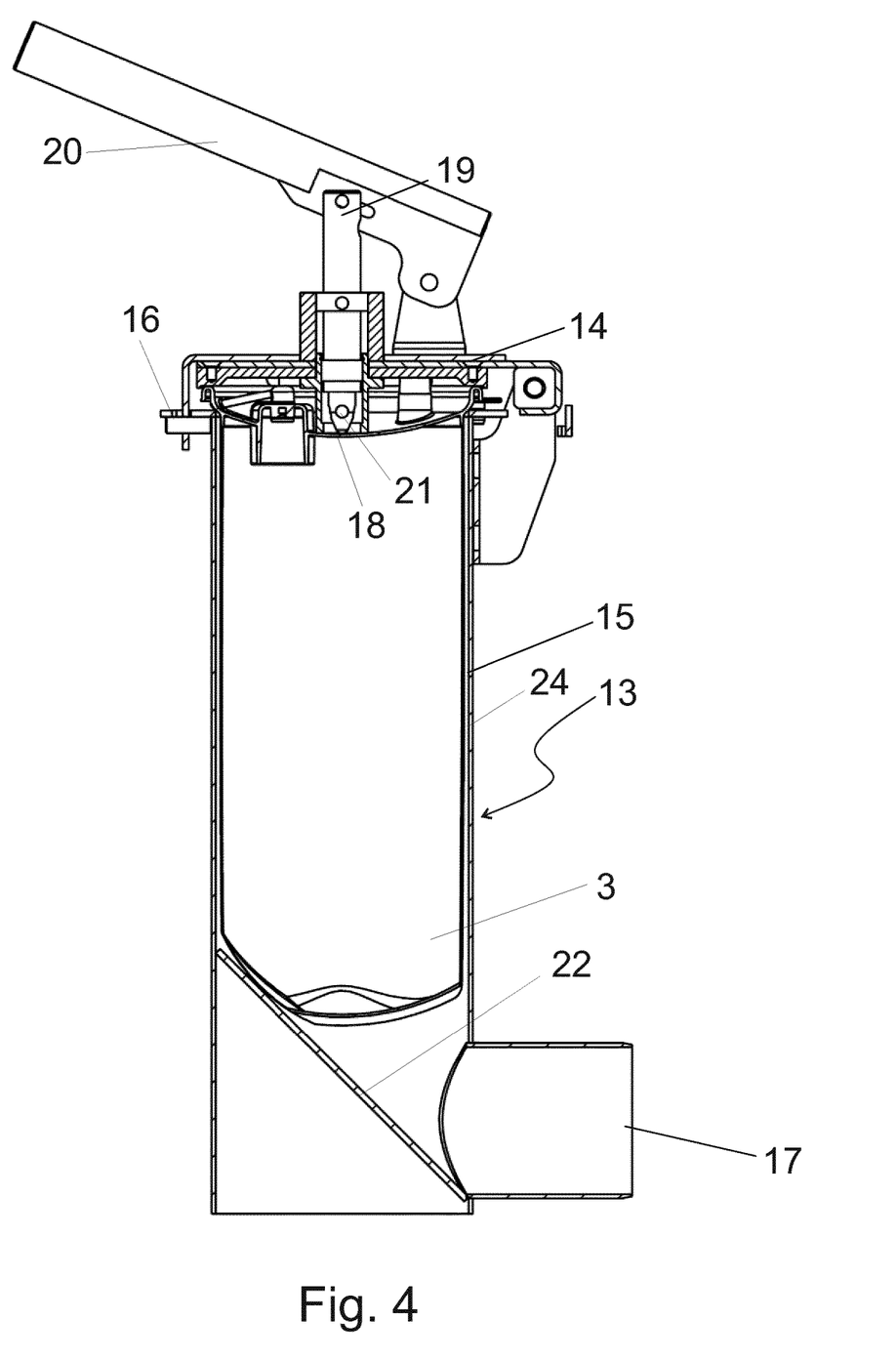
Figure 5:
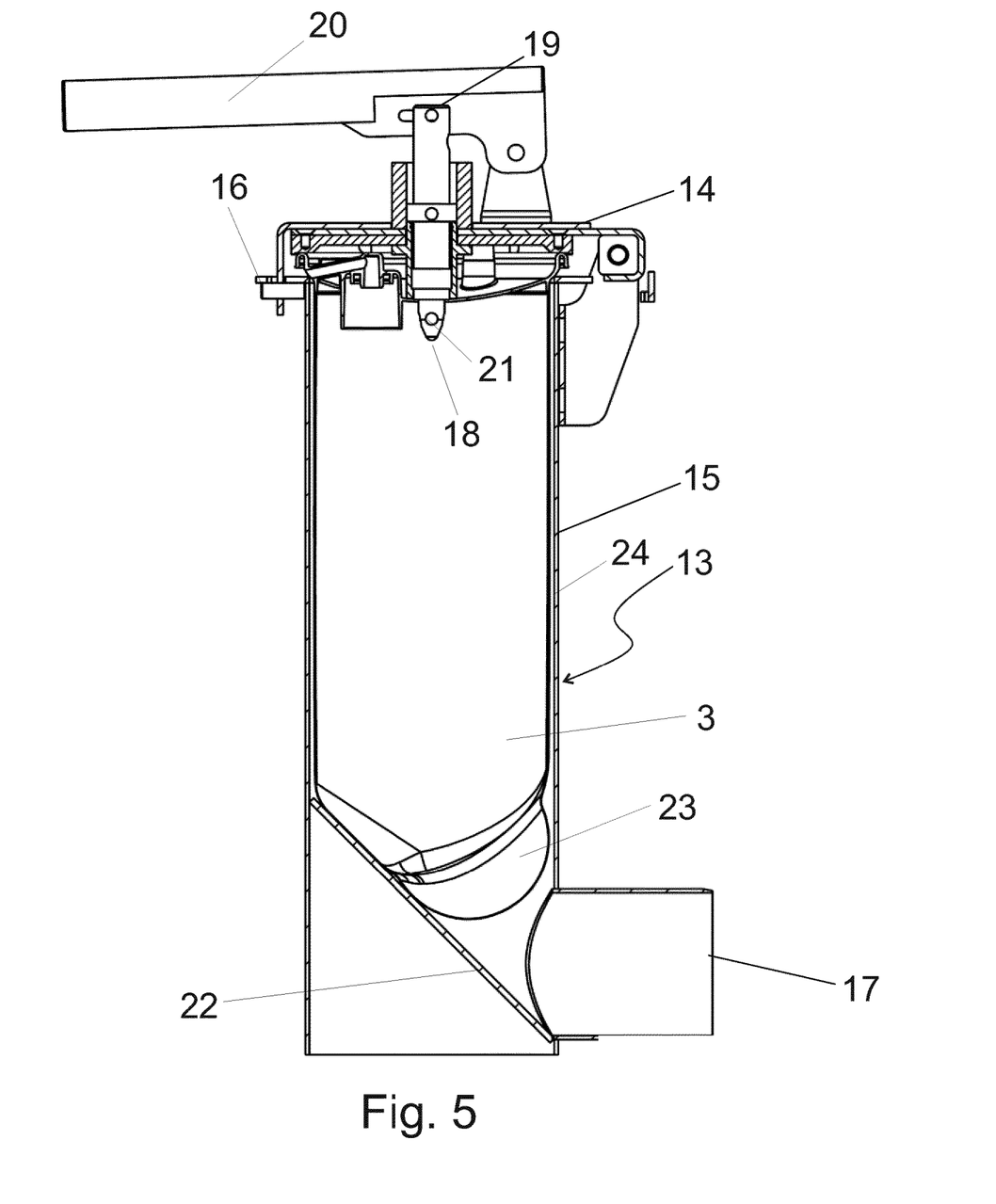

When the suction bag 3 has been set in place in the container 15, the lid 14 of the emptying device 13 is closed by means of a handle 20, as shown in FIG. 4. When the movement of the handle 20 is continued, the blunt conical head 18 of the cylinder 19 punctures the lid 4 of the suction bag 3, as shown in FIG. 5. The hollow cylinder 19 continues through the lid 14 and is connected on the outer surface side of the lid 14 to a source of pressurized gas or liquid. The source of pressurized gas or liquid may be a water supply network or a compressed air network. The source of pressurized gas or liquid may also be used for supplying disinfectant or sterilizer, or a separate container for these agents may be provided, from which they are supplied into the liquid or gas flow. The opening of the source of pressurized gas or liquid may be connected to the closing of the lid 14, in which case the gas or liquid starts to flow automatically through the cylinder 19 into the suction bag 3. In its simplest form the opening of the gas or liquid source may take place by manual opening, for example by opening a water tap.

Figure 6:
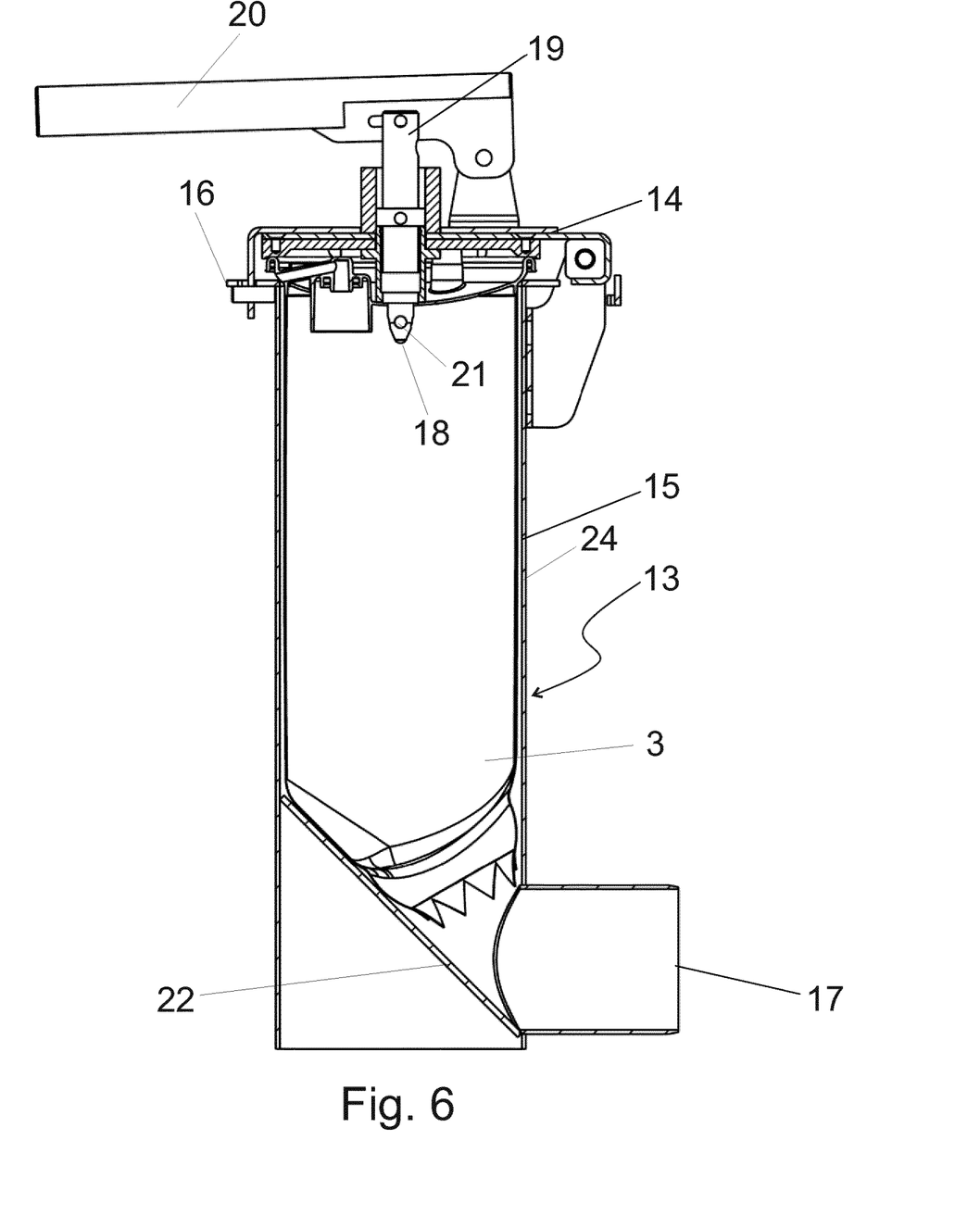

Once the pressurized gas or liquid starts to flow through the lid 4 of the suction bag 3 from the opening punctured by the conical head 18 of the cylinder 19, pressure from the inside of the suction bag 3 starts to act on the suction bag 3. A cylindrical jacket 24 of the container 15 supports the suction bag 3 laterally. The material of the suction bag 3 starts to bulge in the bottom part of the suction bag 3, next to the seam, the bulge being marked in FIG. 5 by reference number 23. As a result of the bulging, the suction bag 3 bursts, as shown in FIG. 6. The contents of the suction bag 3 then flow out of the suction bag 3, first onto the bottom of the container 15 and then out of the container 15 through the discharge point 17. In FIG. 3 the discharge point 17 is shown merely as an opening in the jacket of the container 15, but the discharge point 17 may also be directly coupled to a sewer. There may be at least one guide surface 22 inside the container 15 to guide the flow towards the discharge point 17. When the emptying device has a guide surface 22, the guide surface 22 touches the suction bag 3 on one side of the suction bag 3, while the other side hangs free. The opening in the jacket functions well for example when the entire emptying device 13 is placed in a wash basin with a sewer. The gas or liquid continues to flow through the hollow cylinder 19, and the gas or liquid flow rinses the inside of the suction bag 3. The suction bag 3 is thus emptied completely and the rinsing ensures that the inside of the suction bag 3 becomes entirely cleaned because the gas or liquid flows through the entire suction bag 3 and through the hole formed at the bottom of the suction bag 3 as a result of the bulging.

After the rinsing has continued for a sufficient amount of time, the gas or fluid flow is cut off or the flow shuts off automatically, for example when the lid 14 of the emptying device 13 is opened. The rinsed suction bag 3 can then be removed from the emptying device 13 and taken to waste disposal.

The above description represents one way of puncturing the suction bag but also a non-contact method, such as negative pressure suction, an electric resistor or a laser cutter, may be used for the puncturing. When a non-contact method is used for puncturing the suction bag, the rinsing of the suction bag may be implemented in the way described above.

Figure 7:
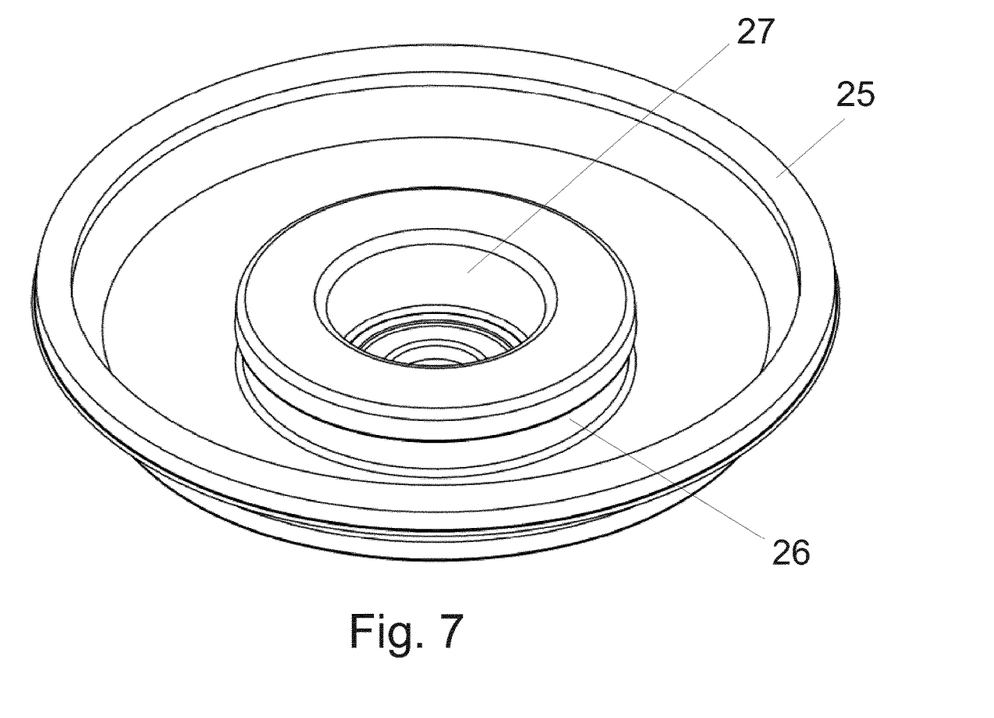
FIG. 7 shows a perspective view of an accessory part, seen obliquely from above.

FIG. 7 shows a perspective view of an accessory part of the suction bag emptying device. The accessory part comprises a lid 25, in the middle of which a container 26 is provided. The container 26 is closed by a plug 27. The lid 25, container 26 and plug 27 are concentric, i.e. in their operation position the vertical axis is the same, and in the case of FIG. 7 they have an annular shape. Other shapes are also feasible. Further, it is feasible that the lid 25, container 26 and plug 27 are not concentric but are positioned in such a way that the container 26 and the plug 27 may be punctured in the manner described above.

Figure 8:
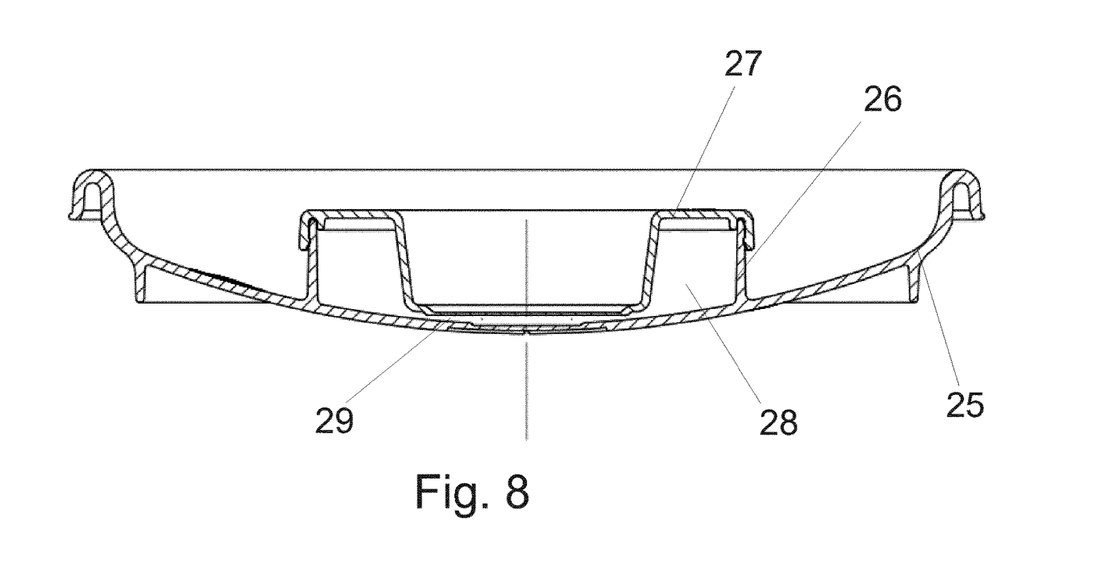
FIG. 8 shows a cross section of an accessory part.

FIG. 8 shows a cross section of the accessory part. As seen in FIG. 8, the lid 25 and the container 26 are a uniform piece. The plug 27 is a separate part which is fastened to the rim of the container 26 after some liquid agent used for cleaning the emptying device has been put in a space 28. When the container 26 has been closed by a plug 27, the agent used for cleaning is in a closed space from where it cannot leak out. The plug 27 is shaped in such a way that its portion to be positioned in the middle of the lid 25 and the container 26 extends into the inside of the container 26 in such a way that it displaces liquid from, the mid-area of the container 26, moving the liquid against the side wall of the container 26. However, between the bottom of the container 26 and the end of the plug 27, in the middle of the container 26 there remains a gap 29 with liquid that is in connection with the liquid on the side wall of the container 26. Inside the container 26, at the bottom, there may be ridges 31 (shown in FIGS. 11 and 12) which prevent the end of the plug 27 from contacting the container bottom. The ridges 31 may extend radially from the mid-point of the container 26 towards the periphery of the container 26.

Figure 9:
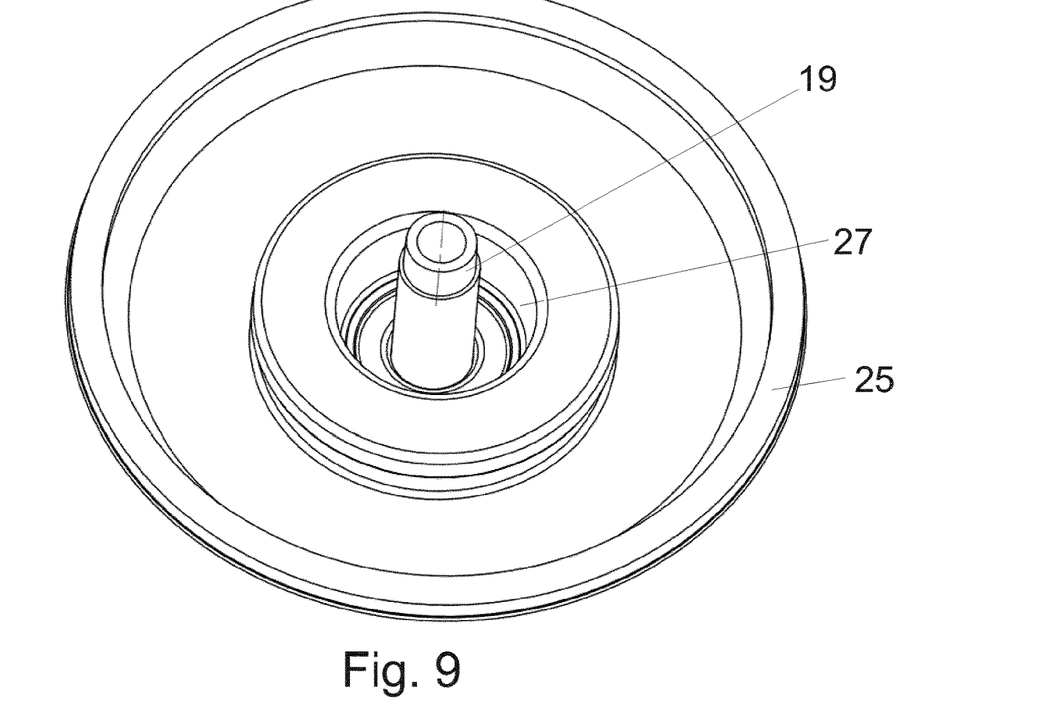
FIG. 9 shows a perspective view of an accessory part, seen obliquely from above.

FIG. 9 shows obliquely from above how the cylinder 19 is pressed through the lid 25 and the plug 27 from the middle of the lid 25.

Figure 10:
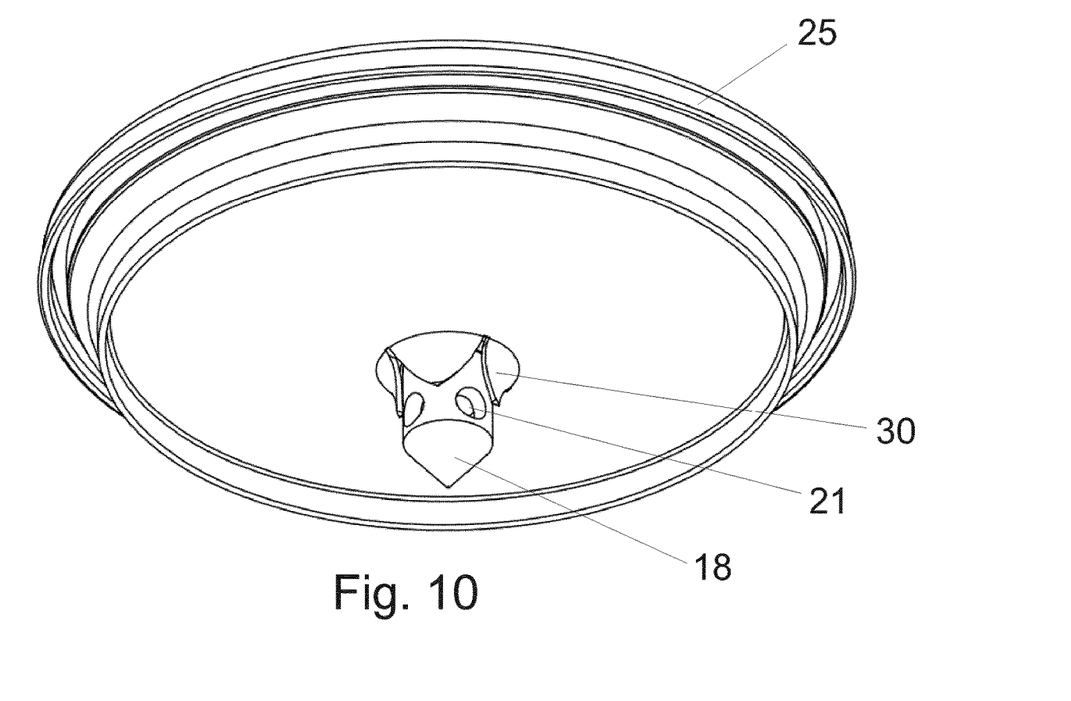
FIG. 10 shows a perspective view of an accessory part, seen obliquely from below.

FIG. 10 shows obliquely from below how the conical head 18 of the cylinder 19, having openings 21, penetrates through the lid 25. The mid-point of the lid 25, i.e. the point where the conical head 18 penetrates the lid 25, is provided with weakenings extending radially away from the mid-point. As the conical head 18 penetrates the lid 25, the material of the lid 25 is torn at the weakenings, and lid strips 30 turn downwards while the cylinder 19 is moving down. Preferably, the lid 25 is weakened in such a way that the openings 21 will be between the strips 30.

Figure 11:
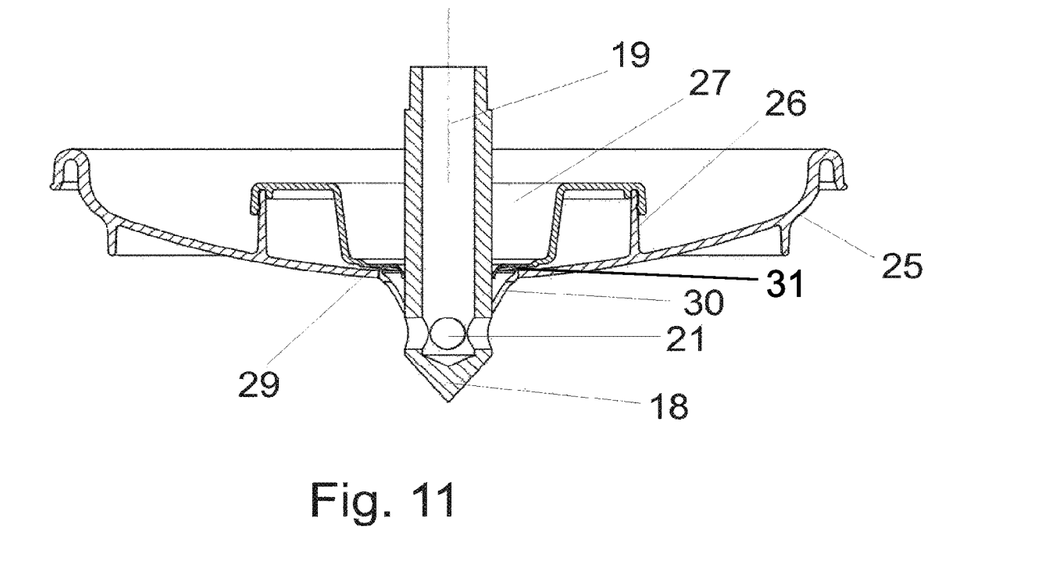
FIG. 11 shows a cross section of an accessory part.
Figure 12:
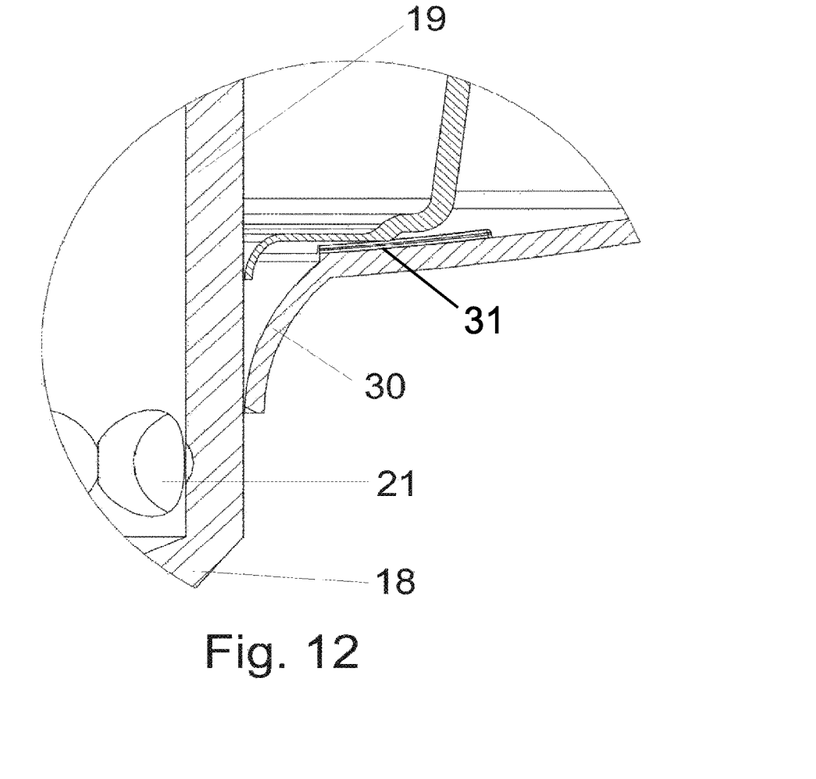
FIG. 12 shows a detail of FIG. 11.

FIG. 11 shows a cross section of the conical head 18 of the cylinder 19 penetrating the lid 25, and FIG. 12 shows an enlargement of a detail. As seen in FIGS. 11 and 12, the ends of the strips 30 are against the cylinder 19. The liquid cleaning agent starts to flow gradually out of the container 26 through the gap 29, through some kind of a funnel formed by the strips 30, to the surface of the conical head 18. As the water or other cleaning liquid starts to flow through the openings 21, the flow takes with it a small amount of cleaning agent all the time, whereby the cleaning agent lasts long enough to ensure a good cleaning result.

It will be obvious to a person skilled in the art that as the technology advances, the basic idea of the invention can be implemented in many different ways. The invention and its embodiments are thus not restricted to the examples described above but may vary within the scope of the claims.

The invention claimed is:

1. An accessory part to be used in connection with cleaning a suction bag emptying device, the accessory part comprising
    a lid for closing a container in the emptying device; and
    a capsule with a cavity formed in the lid for holding a liquid agent to be used for cleaning the emptying device, wherein the cavity is closed by a plug extending to an inside of the cavity, and a gap is disposed between a bottom of the cavity and an end of the plug for throttling liquid flow during cleaning, wherein the bottom of the cavity includes radially extending ridges, and wherein the plug is adapted to displace the liquid agent from a mid-area of the cavity and move the liquid agent against a side wall of the cavity.

2. The accessory part according to claim 1, wherein the lid, cavity and plug are concentric relative to each other.

3. An accessory part to be used in connection with cleaning a suction bag emptying device, the accessory part comprising:
    a lid for closing a container in the emptying device, wherein weakenings extend radially from a mid-point of the lid; and
    a capsule with a cavity formed in the lid for holding a liquid agent to be used for cleaning the emptying device, wherein the cavity is closed by a plug extending to an inside of the cavity, and there is a gap between a bottom of the cavity and an end of the plug for throttling liquid flow during cleaning, wherein the plug is adapted to displace the liquid agent from a mid-area of the cavity and move the liquid agent against a side wall of the cavity.

4. An accessory part to be used in connection with cleaning a suction bag emptying device, the accessory part comprising:
    a lid for closing a container in the emptying device; and
    a capsule with a cavity formed in the lid for holding a liquid agent to be used for cleaning the emptying device, wherein the cavity is closed by a plug extending to the inside of the cavity, and there is a gap between a bottom of the cavity and an end of the plug for throttling liquid flow during cleaning, wherein the plug is adapted to displace the liquid agent from a mid-area of the cavity and move the liquid agent against a side wall of the cavity, and wherein the lid and the cavity are a uniform piece.

* * * * *